(12) United States Patent
Haarsma et al.

(10) Patent No.: US 10,704,058 B2
(45) Date of Patent: Jul. 7, 2020

(54) POWDERY MILDEW RESISTANCE GENES IN CARROT

(71) Applicant: Bejo Zaden B.V., Warmenhuizen (NL)

(72) Inventors: Adriana Dorien Haarsma, Middenmeer (NL); Willem Arie Zwaan, Medemblik (NL); Jurgen Franciscus Nijkamp, Haarlem (NL); Jacobus Petrus Martinus, Alkmaar (NL); Petrus Arnoldus Dekker, Heerhugowaard (NL); Laurentius Petrus Nicolaas Martinus Kroon, Zuidermeer (NL); Albertus Johannes Maria Schrijver, Warmenhuizen (NL)

(73) Assignee: Bejo Zaden B.V., Warmenhuizen (NL)

( * ) Notice: Subject to any disclaimer, the term of this patent is extended or adjusted under 35 U.S.C. 154(b) by 0 days.

(21) Appl. No.: 16/078,124

(22) PCT Filed: Feb. 22, 2016

(86) PCT No.: PCT/EP2016/053667
§ 371 (c)(1),
(2) Date: Aug. 21, 2018

(87) PCT Pub. No.: WO2017/144077
PCT Pub. Date: Aug. 31, 2017

(65) Prior Publication Data
US 2020/0010848 A1    Jan. 9, 2020

(51) Int. Cl.
*A01H 5/10* (2018.01)
*C12N 15/82* (2006.01)

(52) U.S. Cl.
CPC .................. *C12N 15/8282* (2013.01)

(58) Field of Classification Search
None
See application file for complete search history.

(56) References Cited

U.S. PATENT DOCUMENTS

2013/0117880 A1   5/2013   Smith et al.

FOREIGN PATENT DOCUMENTS

| JP | 201115648 A | 1/2011 |
|---|---|---|
| WO | 8607379 A1 | 12/1986 |
| WO | 8907379 A1 | 8/1989 |
| WO | 2012012480 A2 | 1/2012 |

OTHER PUBLICATIONS

Mauricio, 2001, Mapping Quantitative Trait Loci in Plants: Uses and Caveats for Evolutionary Biology, Nature Reviews Genetics 2: 370-381.*
Slate, 2005, Quantitative trait locus mapping in natural populations: progress, caveats and future directions, Molecular Ecology 14: 363-379.*
Gowda et al., 1998, Resistance Source for Powdery Mildew in Carrot, PKV Research Journal 22(1): 55-56.*
Bhat et al, "Petaloid type pers. comm.", Wild Crop Relatives: Genomic and Breeding Resources Millets and Grasses, 2011, p. 106, Springer, Berlin, Germany.
Bioinformatics, "IUPAC Codes", retrieved from http://www.bioinformatics.org/sms/iupac.html.
Braun, "A monograph of the Erysiphales (powdery mildews)", Beihefte zur Nova Hedwigia, 1987, pp. 36-41 and 214-217.
Cavagnaro et al., "A gene-derived SNP-based high resolution linkage map of carrot including the location of QTL conditioning root and leaf anthocyanin pigmentation", BMC Genomics, 2014, vol. 15, Article No. 1118.
Cunnington et al., "First record of powdery mildew on carrots in Australia", Australasian Plant Disease Notes, 2008, pp. 38-41, vol. 3.
Gowda et al., "Resistance Source for Powdery Mildew in Carrot", PKV Research Journal, 1998, pp. 55-56, vol. 22, Issue 1.
Kitagawa et al., "Developmental and morphological analyses of homeotic cytoplasmic male sterile and fertile carrot flowers", Sex Plant Reproduction, 1994, pp. 41-50, vol. 7.
National Institute of Health, "*Daucus carota* subsp. *sativus* cultivar:DH1 Genome sequencing", National Center for Biotechnology Information, Oct. 9, 2015, Version 2, Retrieved from http://www.ncbi.nlm.nih.gov/bioproject/PRJNA268187/.
Parsons et al., "Meloidogyne incognita nematode resistance QTL in carrot", Molecular Breeding, 2015, pp. 1-11, vol. 35, Issue 114.
Simon, "Published DNA Sequences from our laboratory", USDA ARS VCRU Data Server, Jul. 8, 2016, Retrieved from http://www.vcru.wisc.edu/simonlab/sdata/seq/index.html.

(Continued)

*Primary Examiner* — Brastislav Stankovic
(74) *Attorney, Agent, or Firm* — The Webb Law Firm (57) ABSTRACT

Provided herein are carrot plants resistant to powdery mildew, and especially powdery mildew caused by the plant pathogen *Erysiphe heraclei*, wherein the powdery mildew resistance is provided by one or two dominant powdery mildew resistance genes. Also provided herein are molecular markers genetically linked to the present powdery mildew, and especially powdery mildew caused by the plant pathogen *Erysiphe heraclei*, resistance providing genes and the use thereof for identifying carrots plants, or *Daucus carota* plants, being resistant to powdery mildew, and especially powdery mildew caused by the plant pathogen *Erysiphe heraclei*. Also provided herein are seeds, plant parts, pollen, egg cells, callus, suspension culture, somatic embryos and edible plant parts of the present plants.

10 Claims, 3 Drawing Sheets
Specification includes a Sequence Listing.

(56) References Cited

OTHER PUBLICATIONS

Takaichi et al., "Transgenic carrots with enhanced resistance against two major pathogens, *Erysiphe heraclei* and *Alternaria dauci*", Plant Science, 2000, pp. 135-144, vol. 153.
Welch et al., "Male Sterility in the Carrot", Science, 1947, p. 594, vol. 106.
Wikipedia, "Carrot", Wikipedia, Retrieved at https://en.wikipedia.org/wiki/Carrot#cite_note-Zidorn_2005-14.

* cited by examiner

| SEQ ID No. | SNP | position | Sequence (SNP nucleotide is highlighted bold and underlined) |
|---|---|---|---|
| SEQ ID No. 1 | 9620 | 1,654,801 | CTGACCCGACCCGAGACTCGCCGACCTCTTCAACTCCCTCCCTCCAGACATCACCCGACCCGACCCGCCGTCAAACCCGACAAAATCCTCCTCCGACATCG |
| SEQ ID No. 2 | 9624 | 1,661,351 | AATCTTGAAGTTAGTAGCCTTTATTGGCCTTATGCTTGGCAACATCCTGCGGAGACAAATAGGACTATGTACAATAGCAGCAGAATTGCAGTTTTTGATAA |
| SEQ ID No. 3 | 9703 | 1,661,662 | TTCTCAAAAATTCGGAAGAAAATGCAAATGCTTACCWGGGCACAAGATGACCGTTCCAACGGATTGGTCTTATGGATGTGAGCCAGATTTTAAGCCTTCAG |
| SEQ ID No. 4 | 9708 | 1,663,368 | GGTAATGTACTTAAAAAAAAGCACTCCAACACTCTTCTAGTGGTTACTTAGATCACCAGCAYAWYCTCAAATYTCCTAGCCATTACCTATTTATAAGTAAC |
| SEQ ID No. 5 | 9625 | 1,672,079 | GCCTTTGCACTCGAGGGCCGATCTCAGTCCGGTCTGAGGAAATCTTTGCAGGCCTCCGTTAGACCTACGCCCCGTAGAAACTATCATCATGTCCGCTTGCC |
| SEQ ID No. 6 | 9629 | 1,705,739 | CCTAATGACAGGGCTGAAATCTGGGCGGTCCGAAAGGCAAACAGAGCAACCACCGACTCTCGTATATCCTTTCATTCTTCCTGTCCCTCCAATTTTTTAA |
| SEQ ID No. 7 | 9635 | 1,734,335 | GATACTTCAGAGTGCTCAATGAACTTGGCAACGGATCATCTTCGAAGGTTTCTTCGAGAACCAAACCAATTAAGTGACTGGGGTAAGGCACCAAGTCCTTG |
| SEQ ID No. 8 | 9666 | 45,264,585 | TAATAACGTATATATATATGATATGACTTCTAGCACTTGGTTGAAAGATAAAAATCATTGAAACACTTGGTTTGAACCCTTCGATTGAAGATAAGGTCTCT |
| SEQ ID No. 9 | 9669 | 45,290,166 | GCCATTAGAGGAACCAATAACTGTGAACAGGCGCGGCTTAAGTAAATAACTTTTATAGCTGGGACAGACTAGTCGAGTAATGTCTATCAAAACCGATGGTT |
| SEQ ID No. 10 | 9670 | 45,295,089 | TTGAATTCTGCTGTAAACTTGGTCATGTCCTCCTGGTGATGGCACTATTATAATTAACATGGACGGGGCTCTGTTTCATTAAAAGCAGAGTTAATAGTTTC |
| SEQ ID No. 11 | 9671 | 45,302,019 | TACGTCTGTAGTATGAGTGTKTTTTCATGAATTCGGGGTCTGAGATAATACATCGCCACGACTTGCAGACCAAGCTACTCCTCATCAGTGATTTAGCAGGA |
| SEQ ID No. 12 | 9672 | 45,311,025 | CTCTAATACCATTTGTGTTCTAATATTTCTTGTTCAGGTCACTTTACTTTTACATCCTAGGTCTGGTGACCCGTTTCTAAGCTTATCTAGTGATGGTTGTT |
| SEQ ID No. 13 | 6709 | 45,313,919 | ATCCCTGTCAGAAAATTGTTACGTCGGAAAAGAAGGCCTCACGACGCGATCGGAGGAGCTGTAGTAAGAGT |
| SEQ ID No. 14 | 9674 | 45,325,457 | GCAAGTATTACCCAAAATTGGCCCCAATATATATTTTTTGTATCCGGCTATATTGATTGCACCAATGTCACAATCTTGACCAWGAAAAAAGACTCCCTTAA |
| SEQ ID No. 15 | 9677 | 45,350,385 | TGTACGATATATGTTCAGTCTGTTCTTGAGCCTGATTTTACACAATCTTTGAATCCGCGCTGGAAAAATGAAACTTTAGAAGGTTTTCTTTGATCTCTTAA |
| SEQ ID No. 16 | 9620 | 1,654,801 | CTGACCCGACCCGAGACTCGCCGACCTCTTCAACTCCCTCCCTCCAGACACCACCCGACCCGACCCGCCGTCAAACCCGACAAAATCCTCCTCCGACATCG |
| SEQ ID No. 17 | 9624 | 1,661,351 | AATCTTGAAGTTAGTAGCCTTTATTGGCCTTATGCTTGGCAACATCCTGCAGAGACAAATAGGACTATGTACAATAGCAGCAGAATTGCAGTTTTTGATAA |
| SEQ ID No. 18 | 9703 | 1,661,662 | TTCTCAAAAATTCGGAAGAAAATGCAAATGCTTACCWGGGCACAAGATGAACGTTCCAACGGATTGGTCTTATGGATGTGAGCCAGATTTTAAGCCTTCAG |

| SEQ ID No. 19 | 9708 | 1,663,368 | GGTAATGTACTTAAAAAAAAGCACTCCAACACTCTTCTAGTGGTTACTTAAATCACCAGCAYAWYCTCAAATYTCCTAGCCATTACCTATTTATAAGTAAC |
|---|---|---|---|
| SEQ ID No. 20 | 9625 | 1,672,079 | GCCTTTGCACTCGAGGGCCGATCTCAGTCCGGTCTGAGGAAATCTTTGCACGCCTCCGTTAGACCTACGCCCCGTAGAAACTATCATCATGTCCGCTTGCC |
| SEQ ID No. 21 | 9629 | 1,705,739 | CCTAATGACAGGGCTGAAATCTGGGCGGTCCGAAAGGCAAACAGAGCAACTACCGACTCTCGTATATCCTTTCATTCTTCCTGTCCCTCCAATTTTTTTAA |
| SEQ ID No. 22 | 9635 | 1,734,335 | GATACTTCAGAGTGCTCAATGAACTTGGCAACGGATCATCTTCGAAGGTTCCTTCGAGAACCAAACCAATTAAGTGACTGGGGTAAGGCACCAAGTCCTTG |
| SEQ ID No. 23 | 9666 | 45,264,585 | TAATAACGTATATATATATGATATGACTTCTAGCACTTGGTTGAAAGATAGAAATCATTGAAACACTTGGTTTGAACCCTTCGATTGAAGATAAGGTCTCT |
| SEQ ID No. 24 | 9669 | 45,290,166 | GCCATTAGAGGAACCAATAACTGTGAACAGGCGCGGCTTAAGTAAATAACATTTATAGCTGGGACAGACTAGTCGAGTAATGTCTATCAAAACCGATGGTT |
| SEQ ID No. 25 | 9670 | 45,295,089 | TTGAATTCTGCTGTAAACTTGGTCATGTCCTCCTGGTGATGGCACTATTAAAATTAACATGGACGGGGCTCTGTTTCATTAAAAGCAGAGTTAATAGTTTC |
| SEQ ID No. 26 | 9671 | 45,302,019 | TACGTCTGTAGTATGAGTGTKTTTTCATGAATTCGGGGTCTGAGATAATAGATCGCCACGACTTGCAGACCAAGCTACTCCTCATCAGTGATTTAGCAGGA |
| SEQ ID No. 27 | 9672 | 45,311,025 | CTCTAATACCATTTGTGTTCTAATATTTCTTGTTCAGGTCACTTTACTTTGACATCCTAGGTCTGGTGACCCGTTTCTAAGCTTATCTAGTGATGGTTGTT |
| SEQ ID No. 28 | 6709 | 45,313,919 | ATCCCTGTCAGAAAATTGTTACGTCGGAAAAGAAGGCTTCACGACGCGATCGGAGGAGCTGTAGTAAGAGT |
| SEQ ID No. 29 | 9674 | 45,325,457 | GCAAGTATTACCCAAAATTGGCCCCAATATATATTTTTTGTATCCGGCTACATTGATTGCACCAATGTCACAATCTTGACCAWGAAAAAAGACTCCCTTAA |
| SEQ ID No. 30 | 9677 | 45,350,385 | TGTACGATATATGTTCAGTCTGTTCTTGAGCCTGATTTTACACAATCTTTAAATCCGCGCTGGAAAAATGAAACTTTAGAAGGTTTTCTTTGATCTCTTAA |

Cont. of FIGURE 2

POWDERY MILDEW RESISTANCE GENES IN CARROT

CROSS-REFERENCE TO RELATED APPLICATION

This application is the United States national phase of International Application No. PCT/EP2016/053667 filed Feb. 22, 2016, the disclosure of which is hereby incorporated in its entirety by reference.

The Sequence Listing associated with this application is filed in electronic format via EFS-Web and is hereby incorporated by reference into the specification in its entirety. The name of the text file containing the Sequence Listing is 1805622_ST25.txt. The size of the text file is 7,060 bytes, and the text file was created on Aug. 14, 2018.

The present invention relates to powdery mildew, and especially powdery mildew caused by the plant pathogen *Erysiphe heraclei*, resistant carrot plants or *Daucus carota* plants, wherein the powdery mildew resistance is provided by one or two dominant powdery mildew resistance genes. The present invention further relates to molecular markers genetically linked to the present powdery mildew, and especially powdery mildew caused by the plant pathogen *Erysiphe heraclei*, resistance providing genes and the use thereof for identifying carrots plants, or *Daucus carota* plants, being resistant to powdery mildew, and especially powdery mildew caused by the plant pathogen *Erysiphe heraclei*. The present invention also relates to seeds, plant parts, and especially edible plant parts of the present plants.

Carrot, or *Daucus carota*, is a cultivated plant from the Umbelliferae (or Apiaceae) which is common in many parts of the world. The Umbelliferae family consists of many species which are in general aromatic plants with hollow stems; it is between the 20 largest families of flowering plants. Next to the genus *Daucus* other cultivated plants are known; e.g. caraway, celery, coriander, dill, fennel, parsley and parsnip. In total the Umbelliferae encompass more than 3,500 species.

Wild carrot, *Daucus carota* L., is endemic in large parts of the world and has a white taproot which is edible when in a young stage, but becomes woody after prolonged growth. The cultivated carrot, *Daucus carota* and especially *Daucus carota* ssp. *sativus*, is a root vegetable, usually orange but also purple, red, yellow and white varieties are known.

Generally in more moderate climate zones, *Daucus carota* is a biennial plant which has a period of vegetative growth in the first year after sowing; after overwintering the plant will flower in the second year of cultivation. In tropical and subtropical areas carrot has an annual life cycle; the transfer from vegetative to generative stage occurs without vernalization. Further, a few wild species also have an annual life cycle.

Leaves are placed in a spiral composition. When the flower stalk elongates, the tip of the stem gets pointed and becomes a highly branched inflorescence. The stem can reach a length of 60-200 cm.

Flowers are placed in umbels with white, sometimes light green or yellow pedicels; individual flowers are borne on pedicels. The first umbel is present at the end of the main stem, additional umbels will grow from this main branch. Each flower has five petals, five stamens and one central stigma. The flowers are protrandrous, meaning that the anthers release their pollen first, before the stigma of the flower can be pollinated. This mechanism prevents self-pollination to a certain extent and promotes cross pollination. A nectar-containing disc is present at the upper surface of the carpels. The flowers attract pollinating insects, after fertilization the outer part of the umbel bends inward, changing the umbel in a convex, and later a cup shape. Seeds develop in about 30 days and consist of two mericarps, each containing a true seed.

The advent of male sterility in *Daucus* is a character which is very useful for producing hybrid seeds. Two types of male sterility are known in the genus *Daucus*[refs. 1, 2, 3]: the so-called brown anther type (anthers degenerate and shrivel before they can spread pollen) and the petaloid type where stamens are replaced by petal-like structures[ref. 1].

Male sterility observed in carrot is generally cytoplasmic male sterility, meaning that the genetic determinant causing this trait is not located on the nuclear chromosomes but rather is encoded by the mitochondrial DNA. Since mitochondria are transferred to the offspring by egg cells only, this trait is maternally inherited. Since the occurrence of male sterility enables 100% cross pollination, hybrids of *Daucus* are readily produced. Carrot is a crop which suffers from inbreeding depression but heterosis, or hybrid vigour, can be very strong.

Carrot is cultivated for its nutritious taproot. The major part of this root consists of an outer phloem cortex and an inner xylem core. A large proportion of cortex relative to the core is considered to be of high horticultural quality. Many shapes of the taproot are known, depending on usage a round, conical or more cylindrical shape is preferred. Root length varies from 5 to even 40 cm; the diameter can vary from 1 to 10 cm. The colour of the taproot is white in the wild type but cultivated forms are mostly orange, sometimes red, purple, black or yellow. The taproot is rich in carotene, especially ß-carotene, an important anti-oxidant, which can be metabolized to vitamin A. Further, carrots are a source of dietary fibre, vitamins C, B6 and K, and the antioxidant falcarinol. Antioxidants (including carotenoids) have been studied for their ability to prevent chronic disease. Free sugars are mainly sucrose, glucose and fructose.

Cultivation of carrot is performed worldwide. In 2011 more than 35 million tons of carrots were produced[ref. 4]. As is the case with any crop mankind is cultivating, there are also many threats to a good harvest of this crop. Many bacterial, fungal, viral and viroid diseases are known next to many insects and nematodes pests. Major bacterial and fungal diseases are caused by, among others, *Xanthomonas campestris*, *Erwinia carotavora*, *Alternaria dauci*, *Alternaria radicina*, *Pythium* spp., *Rhizoctonia* spp., *Sclerotinia* spp., *Fusarium* spp, *Botrytis cinerea* and *Phytophthora* spp. Nematodes as *Heterodera carotae*, *Meloidogyne* spp. and *Pratylenchus* spp. cause severe damage to the taproot, resulting in yield loss and a product which is unsuitable for marketing. Further a vast array of viruses and viroids is known to have an adverse effect on plant health and yield of carrot.

The reduction in yield of carrot, caused by these pathogens, has led to dedicated breeding programs executed by companies and governmental institutes to introduce resistances against these pathogens. One of the diseases having a major effect on carrot cultivation is *Erysiphe heraclei* causing powdery mildew. *Erysiphe heraclei* belongs to the Ascomyceta, order Erysiphales and causes the foliar disease powdery mildew on several members of the Umbelliferae[ref. 5, 6]. From *E. heraclei*, several formae speciales are known which, in general, are specific to the various genera within this family.

Once infested with *Erysiphe heraclei*, carrot plants become covered with fungus and spores. Haustoria are applied by the fungus to penetrate the plant cells but do not cross the cell membrane; therefore the fungus is present intracellularly. Through these haustoria nutrients and water are absorbed from the extracellular space of the infected plant. Patches of the fungus appear on the lower leaves first, later spreading to the higher plant parts. These blotches spread out to a general colonization of the plant including, if present, the flower stalk. The disease is most severe at temperatures as found in summer and autumn. Severe infection results in loss of foliage, a reduced yield and, in seed crops, a poor seed quality. A yield loss of 20% is not rare. Under moist conditions infected tissue could easily be invaded by other (secondary) pathogens causing a rapid collapse of the foliage. Due to loss of foliage, the affected crop cannot be harvested properly since modern top lifters pull the carrots from the ground by their foliage.

One approach to avoid the effects of an infection by *Erysiphe heraclei* can be the application of fungicides. However, the use of pesticides in general is more and more restrained and also public awareness is in favour of avoiding the application of these compounds. Moreover, organic growers do not apply fungicides in their cultivation. Accordingly, there is a clear need in the art to provide carrots which are resistant against *Erysiphe heraclei*.

In research, conducted by a Japanese institute, an attempt to introduce resistance against *Erysiphe heraclei* was made by a transgenic approach, utilizing a human lysozyme gene under control of the constitutive CaMV 35S promoter. Some transformants showed an improved resistance to *Erysiphe heraclei*. This resistance was confirmed in the offspring[ref. 7].

It is an object of the present invention to partially, if not completely, provide a solution for the above problems of the art with genetic material from *Daucus* germplasm. Specifically, it is an object of the present invention amongst other objects, to provide carrot, or *Daucus carota*, plants being resistant to *Erysiphe heraclei* or to powdery mildew.

The above objects, amongst other objects, are met by providing plants, genes and molecular markers as outlined in the appended claims.

Specifically, the above objects, amongst other objects are, according to a first aspect of the present invention, met by providing *Daucus carota* plants being resistant against powdery mildew caused by the plant pathogen *Erysiphe heraclei*, wherein the resistance is provided by a first resistance gene, or Eh 1, located on chromosome 3 of the plant between SEQ ID No. 4, also designated herein as 9708, and SEQ ID No. 5 also designated herein as 9625.

In the alternative, the above objects, amongst other objects are, according to a first aspect of the present invention, met by providing *Daucus carota* plants being resistant against powdery mildew caused by the plant pathogen *Erysiphe heraclei*, wherein the resistance is provided by a first resistance gene, or Eh 1, located on chromosome 3 of the plant between any one of the molecular markers identified herein as 9618, 9620, 9624, 9703 or 9708 on one side and any one of the molecular markers identified herein as 9625, 9629, 9635, 9631 or 9636 on the other side.

In the alternative, the above objects, amongst other objects are, according to a first aspect of the present invention, met by providing *Daucus carota* plants being resistant against powdery mildew caused by the plant pathogen *Erysiphe heraclei*, wherein the resistance is provided by a first resistance gene, or Eh 1, located on chromosome 3 of the plant between any one of SEQ ID Nos. 1, 2, 3, or 4 on one side and any one of SEQ ID Nos. 5, 6, or 7 on the other side.

The genome of *Daucus carota* has been (partially) sequenced[ref. 8] and this sequence is publically available at NCBI with sequence identification number PRJNA268187[ref 9]. In the sequence of PRJNA268187, the present first resistance gene, or Eh 1, can be found between positions 1,648,619 and 1,739,519 of chromosome 3. Using the sequences presented herein, a skilled person can readily identify the present first resistance gene, or Eh 1, in other publically available sequence information of the genome of *Daucus carota*, and especially chromosome 3 thereof, such as between the position of SEQ ID No. 4 and SEQ ID No. 5 thereon. In the alternative the present first resistance gene, or Eh 1, can be found between any one of SEQ ID Nos. 1, 2, 3, or 4 on one side and any one of SEQ ID Nos. 5, 6, or 7 on the other side.

According to a preferred embodiment of this first aspect of the invention, in the present *Daucus carota* plants, the resistance is further provided by a second resistance gene, or Eh 2, located on chromosome 3 of the plant between SEQ ID No. 11, also designated herein as 9671, and SEQ ID No. 12 also designated herein as 9672.

In the alternative of this preferred embodiment of the present invention, the further resistance is provided by a second resistance gene, or Eh 2, located on chromosome 3 of the plant between any one of the molecular markers identified herein as 9659, 9666, 9669, 9670 or 9671 on one side and any one of the molecular markers identified herein as 9672, 6709, 9674, 9677, 9528, 6909, 4201 or 6069 on the other side.

In the alternative of this preferred embodiment of the present invention, the further resistance is provided by a second resistance gene, or Eh 2, located on chromosome 3 of the plant between any one of SEQ ID Nos. 8, 9, 10, or 11 on one side and any one of SEQ ID Nos. 12, 13, 14, or 15 on the other side.

The genome of *Daucus carota* has been (partially) sequenced and this sequence is publically available at NCBI with sequence identification number PRJNA268187[ref 9]. In the sequence of PRJNA268187, the present second resistance gene, or Eh 2, can be found between positions 45,210,264 and 45,845,221 of chromosome 3. Using the sequences presented herein, a skilled person can readily identify the present second resistance gene, or Eh 2, in other publically available sequence information of the genome of *Daucus carota*, and especially chromosome 3 thereof, such as between the position of SEQ ID No. 11 and SEQ ID No. 12 thereon. In the alternative the present second resistance gene, or Eh 2, can be found between any one of SEQ ID Nos. 8, 9, 10, or 11 on one side and any one of SEQ ID Nos. 12, 13, 14, or 15 on the other side.

According to another preferred embodiment, the present first resistance gene, or Eh 1, is located on chromosome 3 at 2.68 cM and the present second resistance gene, or Eh 2, is located on chromosome 3 at 76.7 cM. As noted above, these chromosome positions in centimorgans correspond to, in the sequence of PRJNA268187, between positions 1,648,619 and 1,739,519 and between 45,210,264 and 45,845,221 of chromosome 3, respectively.

According to yet another preferred embodiment the present first resistance gene, or Eh 1, is obtainable, obtained or derived from seeds of a *Daucus carota* plant deposited on Mar. 19, 2015 under deposit number NCIMB 42389 (Ferguson Building, Craibstone Estate, Bucksburn, Aberdeen AB21 9YA, United Kingdom). Formulated differently, the present first resistance gene, or Eh 1, is, preferably, the resistance gene to be found in seed deposit NCIMB 42389.

According to also yet another preferred embodiment the present second resistance gene, or Eh 2, is obtainable, obtained or derived from seeds of a *Daucus carota* plant deposited on Apr. 16, 2015 under deposit number NCIMB 42397 (Ferguson Building, Craibstone Estate, Bucksburn, Aberdeen AB21 9YA, United Kingdom). Formulated differently, the present second resistance gene, or Eh 2, is, preferably, the resistance gene to be found in seed deposit NCIMB 42397.

According to a preferred embodiment of the present invention, the present first resistance gene, or Eh 1, is identifiable by at least one molecular marker selected from the group consisting of SEQ ID No. 1, SEQ ID No. 2, SEQ ID No. 3, SEQ ID No. 4, SEQ ID No. 5, SEQ ID No. 6, and SEQ ID No. 7. Formulated differently, the present first resistance gene, or Eh 1, is genetically linked to at least one molecular marker selected from the group consisting of SEQ ID No. 1, SEQ ID No. 2, SEQ ID No. 3, SEQ ID No. 4, SEQ ID No. 5, SEQ ID No. 6, and SEQ ID No. 7.

According to a further preferred embodiment of the present invention, the present second resistance gene, or Eh 2, is identifiable by at least one molecular marker selected from the group consisting of SEQ ID No. 8, SEQ ID No. 9, SEQ ID No. 10, SEQ ID No. 11, SEQ ID No. 12, SEQ ID No. 13, SEQ ID No. 14, and SEQ ID No. 15. Formulated differently, the present second resistance gene, or Eh 2, is genetically linked to at least one molecular marker selected from the group consisting of SEQ ID No. 8, SEQ ID No. 9, SEQ ID No. 10, SEQ ID No. 11, SEQ ID No. 12, SEQ ID No. 13, SEQ ID No. 14, and SEQ ID No. 15.

Considering the genetic linkage between the present first resistance gene, or Eh 1 and the present molecular markers, the present invention, according to an especially preferred embodiment, relates to *Daucus carota* plants comprising in their genomes at least one genomic sequence selected from the group consisting of SEQ ID No. 1, SEQ ID No. 2, SEQ ID No. 3, SEQ ID No. 4, SEQ ID No. 5, SEQ ID No. 6, and SEQ ID No. 7.

Considering the genetic linkage between the present second resistance gene, or Eh 2 and the present molecular markers, the present invention, according to an especially preferred embodiment, relates to *Daucus carota* plants comprising in their genomes at least one genomic sequence selected from the group consisting of SEQ ID No. 8, SEQ ID No. 9, SEQ ID No. 10, SEQ ID No. 11, SEQ ID No. 12, SEQ ID No. 13, SEQ ID No. 14, and SEQ ID No. 15.

According to a most preferred embodiment, the present invention relates to *Daucus carota* plants comprising in their genomes at least one genomic sequence selected from the group consisting of SEQ ID No. 1, SEQ ID No. 2, SEQ ID No. 3, SEQ ID No. 4, SEQ ID No. 5, SEQ ID No. 6, and SEQ ID No. 7 and at least one genomic sequence selected from the group consisting of SEQ ID No. 8, SEQ ID No. 9, SEQ ID No. 10, SEQ ID No. 11, SEQ ID No. 12, SEQ ID No. 13, SEQ ID No. 14, and SEQ ID No. 15.

The plants as defined above are preferably hybrid plants, more preferably sterile hybrid plants and most preferably male sterile hybrid plants such as a cytoplasmic male sterile.

The present *Daucus carota* plants are preferably *Daucus carota* ssp. *sativus* plants.

According to another aspect, the present invention relates to seeds, edible parts pollen, egg cells, callus, suspension culture, (somatic) embryos or plant parts of a *Daucus carota* plant as defined above.

Considering the genetic linkage between the present molecular markers and the present resistance genes Eh 1 and Eh 2, the present invention relates to, according to still another aspect, the use of one or more molecular markers selected from the group consisting of SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, and SEQ ID No. 15 for identifying a *Daucus carota* plant being resistant against powdery mildew caused by the plant pathogen *Erysiphe heraclei*.

Still considering the genetic linkage between the present molecular markers and the present resistance genes Eh 1 and Eh 2, the present invention relates to, according to yet another aspect, a gene providing resistance against powdery mildew caused by the plant pathogen *Erysiphe heraclei* the gene is located on chromosome 3 at 2.6 cM and the gene is identifiable by at least one molecular marker selected from the group consisting of SEQ ID No. 1, SEQ ID No. 2, SEQ ID No. 3, SEQ ID No. 4, SEQ ID No. 5, SEQ ID No. 6, and SEQ ID No. 7 and to a gene located on chromosome 3 at 76.7 cM and the gene is identifiable by at least one molecular marker selected from the group consisting of SEQ ID No. 8, SEQ ID No. 9, SEQ ID No. 10, SEQ ID No. 11, SEQ ID No. 12, SEQ ID No. 13, SEQ ID No. 14, and SEQ ID No. 15.

The present invention will be further detailed in the following examples and figures wherein:

FIG. 2: shows sequences of the molecular markers SNP markers as shown in FIG. 1 and their position on chromosome 2 of the sequence of PRJNA268187[ref. 9].

SEQ ID No. 1-7 correspond with the SNP representing the resistant gene at locus Eh 1

SEQ ID No. 8-15 correspond with the SNP representing the resistant gene at locus Eh 2

SEQ ID No. 16-22 correspond with the SNP representing the susceptible gene at locus Eh 1

SEQ ID No. 23-30 correspond with the SNP representing the susceptible gene at locus Eh 2

Code usage according to the IUPAC nucleotide code[ref 10]:

| | |
|---|---|
| A = adenine | T = thymine |
| C = cytosine | G = guanine |
| K = G or T | |
| W = A or T | |
| Y = C or T | |

EXAMPLES

Example 1: Testing for Resistance Against *Erysiphe heraclei* in the Glasshouse

The fungus, as obligate parasite, was maintained on suitable susceptible carrot plants by placing infected leaves between them. Infection was spread among these plants by using a fan, by the air currents the spores were distributed among the plants.

Plants to be tested for resistance were sown in soil on tables, around 30 plants per row. Every 20 rows of plants to be assessed a row of resistant material for race 0 and race 1 and susceptible material each were inserted. When the plants were about 3 cm tall, inoculation took place by adding infected leaves, clearly showing fungal spores. Plants to be assayed for resistance were stroked first with these leaves, and then the inoculating leaves were placed between the young plants. Spores were spread further using a fan. Temperature was 16±2° C. at night; 22±2° C. during daytime; min. 16 hours light (or more if day length was longer) and max. 8 hours dark. Humidity was kept at a high level by spraying water between the tables a few times a week. After 6 weeks the plants were evaluated; infected leaves were covered with a white powdery mycelium and spores, and often turn chlorotic.

The severity of infection was reflected by scoring the symptoms between 0 (completely susceptible) and 9 (completely resistant). It was carefully checked that the susceptible control plants are indeed showing the symptoms of *E. heraclei* infection.

Example 2: Field Tests for Resistance Against *E. heraclei*

Field tests were performed under Dutch climatological conditions. The fungal inoculum was prepared as described above in Example 1. Material to be tested in the field is directly sown during the first half of May.

When plants were about 3 cm tall, the inoculum was spread by placing pots with sporulating plants in the field between the young materials to be tested. The wind will spread spores from the inoculating plants.

Plants were assessed for their resistance or susceptibility when symptoms were clearly visible during dry weather conditions. The severity of infection was reflected by scoring the symptoms between 0 (completely susceptible) and 9 (completely resistant).

Example 3: Molecular Characterization of Genomic DNA and Mapping of the Resistance Genes Applying the two available genetic resources for resistance described above, two F1S1 populations were made by crossing the different sources of resistance to a susceptible carrot line, after which the resulting F1 plant was self-pollinated. The observed segregation of three resistant plants to one susceptible plant learned that indeed in both cases the resistance is based on a dominant trait.

Basic research lead to a partial genetic map of *D. carota* and also a near-complete sequence of its genome, submitted to NCBI as project PRJNA268187[ref. 9].

At least 2000 seeds were harvested from the F1S1 generation of a cross between the distinctive sources of resistance and a susceptible carrot line. To perform a QTL mapping, 1200 plants of each cross were grown in the glasshouse. From each individual plant, leaf material was used for DNA isolation and successive marker analysis.

Inbreds of selected individuals with crossovers nearby the resistance locus were tested in the greenhouse as described in example 1 and resistance was confirmed.

To develop more single nucleotide polymorphic (SNP) markers in the region of the resistance gene, a sequence project was started with the available sources of resistance against *E. heraclei*.

Using SNP markers covering the entire genome, both resistance genes were determined to be located on chromosome 3. Using sequences of the two resistance lines and one susceptible line, in combination with the genome sequence available, for both resistance loci many SNPs were discovered. Based on crossovers present in the mapping populations, each resistance locus could be located on the genome sequence, submitted to NCBI as PRJNA268187[ref. 9].

For *D. carota* accession NCIMB42389 the resistance locus (Eh 1) was located on chromosome 3 at 2.68 cM, corresponding to a fragment between position 1,648,619 and 1,739,519 bp.

By using the sequences described above, more SNP markers have been developed in the region of the resistance locus and used to genotype the resistance sources and the individuals with a crossover near the resistance locus, see Table 1 below:

| marker | physical position | NCIMB42389 | Susceptible | S9342-13 | S9342-19 | S9342-05 | S9342-12 | S9342-21 | S9342-22 | S9342-09 | S9342-25 | S9342-01 | S9342-04 | S9342-18 | S9342-02 | S9342-03 |
|---|---|---|---|---|---|---|---|---|---|---|---|---|---|---|---|---|
| 9618 | CHR3: 1,648,619 | a | b | b | h | h | h | h | h | h | h | h | h | b | b | b |
| 9620 | CHR3: 1,654,801 | a | b | h | h | h | h | h | h | h | h | h | h | b | b | b |
| 9624 | CHR3: 1,661,351 | a | b | h | h | h | h | h | h | h | h | h | h | b | b | b |
| 9703 | CHR3: 1,661,662 | a | b | h | h | h | h | h | h | h | h | h | h | b | b | b |
| 9708 | CHR3: 1,663,368 | a | b | h | h | h | h | h | h | h | h | h | h | b | b | b |
| disease test | | r | s | r | r | r | r | r | r | r | r | r | r | s | s | s |
| 9625 | CHR3: 1,672,079 | a | b | h | h | h | h | h | h | h | h | h | h | b | b | b |
| 9629 | CHR3: 1,705,739 | a | b | h | h | h | h | h | h | h | h | h | h | b | b | b |
| 9635 | CHR3: 1,734,335 | a | b | h | h | h | h | h | h | h | h | h | h | b | b | b |
| 9631* | CHR3: 1,722,613 | a | b | h | h | h | h | b | | | | | | | | |
| 9636 | CHR3: 1,739,519 | a | b | h | h | h | h | b | | | | | | | | |

| | | | | | | | |
|---|---|---|---|---|---|---|---|
| 9631* | h | h | h | h | h | b | b | b |
| 9636 | h | h | h | h | h | b | b | b |

*regarding to marker 9631: based on crossover data, the physical map in this region was corrected for the order of markers The resistance locus is located between markers 9618 and 9631.

Further, for *D. carota* accession NCIMB42397 the location of the second resistance locus (Eh 2) was determined on chromosome 3 around 76.7 cM, corresponding to a fragment between positions 45,210,264 bp and 45,845,221 bp$^{(ref\ 9)}$.

Also for genotype accession NCIMB42397 more markers could be developed with the information from the sequence project and used to genotype accession NCIMB42397 and individuals with a crossover, see Table 2 below:

| marker | physical position | NCIMB42397 | susceptible | Individual F1S1 plants | | | |
|---|---|---|---|---|---|---|---|
| | | | | T9067-4 | T9067-5 | T9067-6 | T9067-17 |
| 9659 | CHR3: 45,210,264 | a | b | h | h | h | h |
| 9666 | CHR3: 45,264,585 | a | b | h | h | h | h |
| 9669 | CHR3: 45,290,166 | a | b | h | h | h | h |
| 9670 | CHR3: 45,295,089 | a | b | h | h | h | h |
| 9671 | CHR3: 45,302,019 | a | b | h | h | h | h |
| disease test | | r | s | r | r | r | r |
| 9672 | CHR3: 45,311,025 | a | b | h | h | h | h |
| 6709 | CHR3: 45,313,919 | a | b | h | h | h | h |
| 9674 | CHR3: 45,325,457 | a | b | h | h | h | h |
| 9677 | CHR3: 45,350,385 | a | b | h | h | h | h |
| 9528 | CHR3: 45,397,477 | a | b | h | h | h | h |
| 6909 | CHR3: 45,399,809 | a | b | h | h | h | h |
| 4201 | CHR3: 45,418,720 | a | b | h | h | h | h |
| 6069 | CHR3: 45,845,221 | a | b | h | h | h | h |

| marker | Individual F1S1 plants | | | | | | | |
|---|---|---|---|---|---|---|---|---|
| | T9067-18 | T9067-19 | T9067-20 | T9067-7 | T9067-8 | T9067-11 | T9067-13 | T9067-16 |
| 9659 | h | h | h | h | h | b | b | b |
| 9666 | h | h | h | b | b | b | b | b |
| 9669 | h | h | h | b | b | b | b | b |
| 9670 | h | h | h | b | b | b | b | b |
| 9671 | h | h | h | b | b | b | b | b |
| disease test | r | r | r | s | s | s | s | s |
| 9672 | h | h | h | b | b | b | b | b |
| 6709 | h | h | h | b | b | b | b | b |
| 9674 | h | h | h | b | b | b | b | b |
| 9677 | h | h | h | b | b | b | b | b |
| 9528 | h | h | h | b | b | b | b | b |
| 6909 | h | h | h | b | b | b | b | b |
| 4201 | h | h | h | b | b | b | b | b |
| 6069 | h | h | b | b | b | h | h | b |

Figure 1:
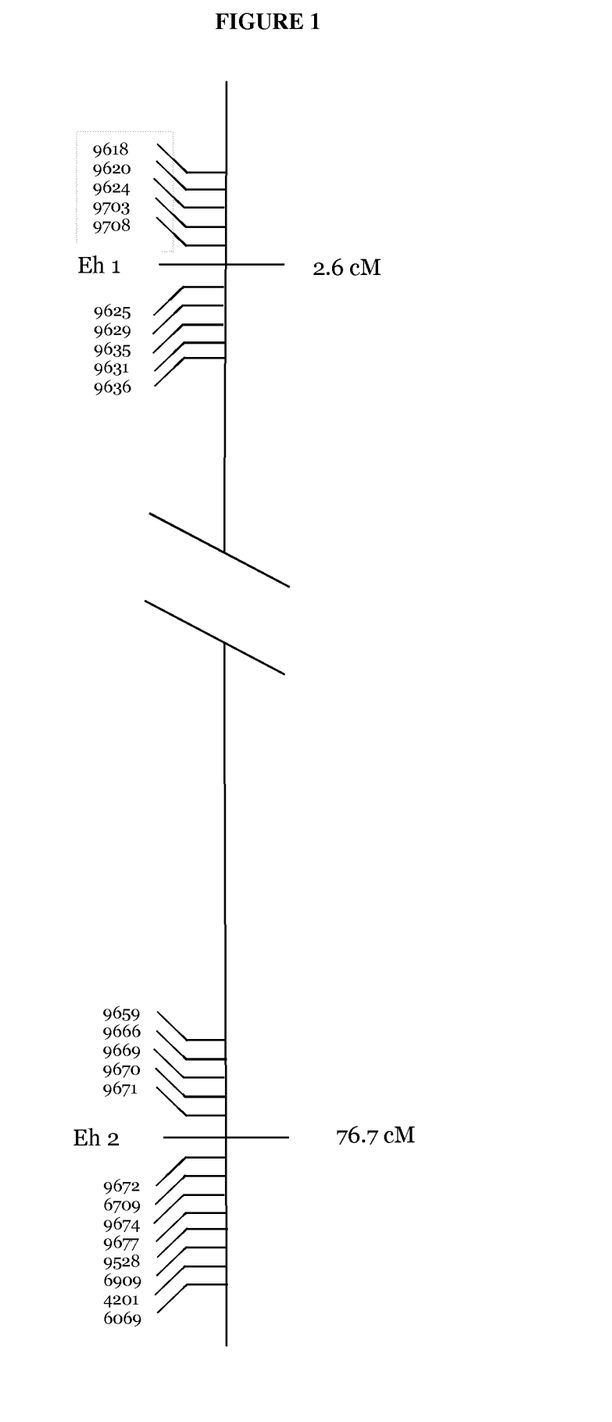
FIG. 1: shows a schematic physical map of chromosome 3 of *Daucus carota* showing both the present molecular markers and the present first resistance gene Eh 1 and the present second resistance gene Eh 2 providing resistance to the plant pathogen *Erysiphe heraclei*.

As graph this situation can alternatively be illustrated as in FIG. 1.

As is clear both from the position in cM and base pair position and illustrated by FIG. 1, the present dominant resistance genes involved are located far apart on chromosome 3. This discovery of two separate resistance genes means that these resistance genes preferably can be stacked e.g. in a hybrid to have a more solid genetic base for a durable resistance.

Deposit Information

Seed samples of the sources of resistance mentioned above were deposited at the NCIMB, Ferguson Building; Craibstone Estate, Bucksburn, Aberdeen, Scotland, AB21 9YA, as:

NCIMB 42389 (*D. carota* #954561), Mar. 19, 2015
NCIMB 42397 (*D. carota* #1360572), Apr. 16, 2015

REFERENCES

1. Kitagawa, J., U. Posluszny, J. M. Gerrath and D. J. Wolyn. Developmental and morphological analyses of homeotic cytoplasmic male sterile and fertile carrot flowers. Sex. Plant Reprod. 7: 4150 (1994)
2. Welch J. E., Grimball E. L. Male sterility in the carrot. Science. 1947. Vol. 106, N2 2763 p. 594
3. Munger, H. Petaloid type pers. comm. Cited in: Wild Crop Relatives: Genomic and Breeding Resources Vegetables; edited by C. Kole. Springer. ISBN 978-3-642-20450-0 p. 106. (2011)
4. Braun U (1987) A monograph of the Erysiphales (powdery mildews). Beiheft zur Nova Hedwigia 89, 1-700.
5. Cunnington J H, Watson A, Liberato J R, Jones R (2008) First record of powdery mildew on carrots in Australia. Australasian Plant Disease Notes 3, 38-41.
6. Takaichi, M. and K. Oeda. Transgenic carrots with enhanced resistance against two major pathogens, *Erysiphe heraclei* and *Alternaria dauci*. Plant Sci. 153: 135 144 (2000)

The invention claimed is:

1. A *Daucus carota* plant that is resistant to powdery mildew caused by the plant pathogen *Erysiphe heraclei* and comprising in its genome SEQ ID NO: 4 and SEQ ID NO: 5, representative seed of said plant having been deposited under NCIMB Accession No. 42389, wherein said plant is a hybrid plant.

2. The *Daucus carota* plant according to claim 1, further comprising in its genome SEQ ID NO: 11 and SEQ ID NO: 12.

3. The *Daucus carota* plant according to claim 1, wherein SEQ ID NO: 4 and SEQ ID NO: 5 are located on chromosome 3 at 2.68 cM.

4. The *Daucus carota* plant according to claim 2, wherein SEQ ID NO: 11 and SEQ ID NO: 12 are located on chromosome 3 at 76.7 cM.

5. The *Daucus carota* plant according to claim 2, wherein representative seed of said plant having been deposited under deposit number NCIMB 42397.

6. The *Daucus carota* plant according to claim 1, wherein said hybrid plant is a sterile hybrid plant.

7. The *Daucus carota* plant according to claim 6, wherein said sterile hybrid plant is a sterile male.

8. The *Daucus carota* plant according to claim 1, wherein said plant is *Daucus carota* ssp. *sativus*.

9. Seeds, edible parts, pollen, egg cells, callus, suspension culture, somatic embryos, embryos or plant parts of a *Daucus carota* plant according to claim 1, wherein the seeds, edible parts, pollen, egg cells, callus, suspension culture, somatic embryos, embryos or plant parts comprise SEQ ID NO:4 and SEQ ID NO:5.

10. The *Daucus carota* plant according to claim 7, wherein said sterile male plant is a cytoplasmic sterile male hybrid plant.

* * * * *

SEQUENCE LISTING

<160> NUMBER OF SEQ ID NOS: 30

<210> SEQ ID NO 1
<211> LENGTH: 101
<212> TYPE: DNA
<213> ORGANISM: Daucus carota

<400> SEQUENCE: 1
ctgacccgac ccgagactcg ccgacctctt caactccctc cctccagaca tcacccgacc    60
cgacccgccg tcaaacccga caaaatcctc ctccgacatc g                       101

<210> SEQ ID NO 2
<211> LENGTH: 101
<212> TYPE: DNA
<213> ORGANISM: Daucus carota

<400> SEQUENCE: 2
aatcttgaag ttagtagcct ttattggcct tatgcttggc aacatcctgc ggagacaaat    60
aggactatgt acaatagcag cagaattgca gttttttgata a                      101

<210> SEQ ID NO 3
<211> LENGTH: 101
<212> TYPE: DNA
<213> ORGANISM: Daucus carota

<400> SEQUENCE: 3
ttctcaaaaa ttcggaagaa aatgcaaatg cttaccwggg cacaagatga ccgttccaac    60
ggattggtct tatggatgtg agccagattt taagccttca g                       101

<210> SEQ ID NO 4
<211> LENGTH: 101
<212> TYPE: DNA
<213> ORGANISM: Daucus carota

<400> SEQUENCE: 4
ggtaatgtac ttaaaaaaaa gcactccaac actcttctag tggttactta gatcaccagc    60
ayawyctcaa atytcctagc cattacctat ttataagtaa c                       101

<210> SEQ ID NO 5
<211> LENGTH: 101
<212> TYPE: DNA
<213> ORGANISM: Daucus carota

<400> SEQUENCE: 5
gcctttgcac tcgagggccg atctcagtcc ggtctgagga aatctttgca ggcctccgtt    60
agacctacgc cccgtagaaa ctatcatcat gtccgcttgc c                       101

<210> SEQ ID NO 6
<211> LENGTH: 101
<212> TYPE: DNA
<213> ORGANISM: Daucus carota

<400> SEQUENCE: 6
cctaatgaca gggctgaaat ctgggcggtc cgaaaggcaa acagagcaac caccgactct    60
cgtatatcct ttcattcttc ctgtccctcc aattttttta a                       101

<210> SEQ ID NO 7
<211> LENGTH: 101
<212> TYPE: DNA
<213> ORGANISM: Daucus carota

<400> SEQUENCE: 7
gatacttcag agtgctcaat gaacttggca acggatcatc ttcgaaggtt tcttcgagaa    60
ccaaaccaat taagtgactg gggtaaggca ccaagtcctt g                        101

<210> SEQ ID NO 8
<211> LENGTH: 101
<212> TYPE: DNA
<213> ORGANISM: Daucus carota

<400> SEQUENCE: 8
taataacgta tatatatatg atatgacttc tagcacttgg ttgaaagata aaaatcattg    60
aaacacttgg tttgaaccct tcgattgaag ataaggtctc t                        101

<210> SEQ ID NO 9
<211> LENGTH: 101
<212> TYPE: DNA
<213> ORGANISM: Daucus carota

<400> SEQUENCE: 9
gccattagag gaaccaataa ctgtgaacag gcgcggctta agtaaataac ttttatagct    60
gggacagact agtcgagtaa tgtctatcaa aaccgatggt t                        101

<210> SEQ ID NO 10
<211> LENGTH: 101
<212> TYPE: DNA
<213> ORGANISM: Daucus carota

<400> SEQUENCE: 10
ttgaattctg ctgtaaactt ggtcatgtcc tcctggtgat ggcactatta taattaacat    60
ggacggggct ctgtttcatt aaaagcagag ttaatagttt c                        101

<210> SEQ ID NO 11
<211> LENGTH: 101
<212> TYPE: DNA
<213> ORGANISM: Daucus carota

<400> SEQUENCE: 11
tacgtctgta gtatgagtgt kttttcatga attcggggtc tgagataata catcgccacg    60
acttgcagac caagctactc ctcatcagtg atttagcagg a                        101

<210> SEQ ID NO 12
<211> LENGTH: 101
<212> TYPE: DNA
<213> ORGANISM: Daucus carota

<400> SEQUENCE: 12
ctctaatacc atttgtgttc taatatttct tgttcaggtc actttacttt tacatcctag    60
gtctggtgac ccgtttctaa gcttatctag tgatggttgt t                        101

<210> SEQ ID NO 13
<211> LENGTH: 71
<212> TYPE: DNA
<213> ORGANISM: Daucus carota

<400> SEQUENCE: 13
atccctgtca gaaaattgtt acgtcggaaa agaaggcctc acgacgcgat cggaggagct    60
gtagtaagag t                                                          71

<210> SEQ ID NO 14
<211> LENGTH: 101
<212> TYPE: DNA
<213> ORGANISM: Daucus carota

<400> SEQUENCE: 14
gcaagtatta cccaaaattg gccccaatat atatttttg tatccggcta tattgattgc    60
accaatgtca caatcttgac cawgaaaaaa gactcccttt a                        101

<210> SEQ ID NO 15
<211> LENGTH: 101
<212> TYPE: DNA
<213> ORGANISM: Daucus carota

<400> SEQUENCE: 15
tgtacgatat atgttcagtc tgttcttgag cctgatttta cacaatcttt gaatccgcgc    60
tggaaaaatg aaactttaga aggttttctt tgatctctta a                        101

<210> SEQ ID NO 16
<211> LENGTH: 101
<212> TYPE: DNA
<213> ORGANISM: Daucus carota

<400> SEQUENCE: 16
ctgacccgac ccgagactcg ccgacctctt caactccctc cctccagaca ccacccgacc    60
cgacccgccg tcaaacccga caaaatcctc ctccgacatc g                        101

<210> SEQ ID NO 17
<211> LENGTH: 101
<212> TYPE: DNA
<213> ORGANISM: Daucus carota

<400> SEQUENCE: 17
aatcttgaag ttagtagcct ttattggcct tatgcttggc aacatcctgc agagacaaat    60
aggactatgt acaatagcag cagaattgca gttttgata a                         101

<210> SEQ ID NO 18
<211> LENGTH: 101
<212> TYPE: DNA
<213> ORGANISM: Daucus carota

<400> SEQUENCE: 18
ttctcaaaaa ttcggaagaa aatgcaaatg cttaccwggg cacaagatga acgttccaac    60
ggattggtct tatggatgtg agccagattt taagccttca g                        101

<210> SEQ ID NO 19
<211> LENGTH: 101
<212> TYPE: DNA
<213> ORGANISM: Daucus carota

<400> SEQUENCE: 19
ggtaatgtac ttaaaaaaaa gcactccaac actcttctag tggttactta aatcaccagc    60
ayawyctcaa atytcctagc cattacctat ttataagtaa c                        101

<210> SEQ ID NO 20
<211> LENGTH: 101
<212> TYPE: DNA
<213> ORGANISM: Daucus carota

<400> SEQUENCE: 20

```
gcctttgcac tcgagggccg atctcagtcc ggtctgagga aatctttgca cgcctccgtt    60
agacctacgc cccgtagaaa ctatcatcat gtccgcttgc c                        101

<210> SEQ ID NO 21
<211> LENGTH: 101
<212> TYPE: DNA
<213> ORGANISM: Daucus carota

<400> SEQUENCE: 21
cctaatgaca gggctgaaat ctgggcggtc cgaaaggcaa acagagcaac taccgactct    60
cgtatatcct ttcattcttc ctgtccctcc aattttttta a                        101

<210> SEQ ID NO 22
<211> LENGTH: 101
<212> TYPE: DNA
<213> ORGANISM: Daucus carota

<400> SEQUENCE: 22
gatacttcag agtgctcaat gaacttggca acggatcatc ttcgaaggtt ccttcgagaa    60
ccaaaccaat taagtgactg gggtaaggca ccaagtcctt g                        101

<210> SEQ ID NO 23
<211> LENGTH: 101
<212> TYPE: DNA
<213> ORGANISM: Daucus carota

<400> SEQUENCE: 23
taataacgta tatatatatg atatgacttc tagcacttgg ttgaaagata gaaatcattg    60
aaacacttgg tttgaacccct tcgattgaag ataaggtctc t                       101

<210> SEQ ID NO 24
<211> LENGTH: 101
<212> TYPE: DNA
<213> ORGANISM: Daucus carota

<400> SEQUENCE: 24
gccattagag gaaccaataa ctgtgaacag gcgcggctta agtaaataac atttatagct    60
gggacagact agtcgagtaa tgtctatcaa aaccgatggt t                        101

<210> SEQ ID NO 25
<211> LENGTH: 101
<212> TYPE: DNA
<213> ORGANISM: Daucus carota

<400> SEQUENCE: 25
ttgaattctg ctgtaaactt ggtcatgtcc tcctggtgat ggcactatta aaattaacat    60
ggacggggct ctgtttcatt aaaagcagag ttaatagttt c                        101

<210> SEQ ID NO 26
<211> LENGTH: 101
<212> TYPE: DNA
<213> ORGANISM: Daucus carota

<400> SEQUENCE: 26
tacgtctgta gtatgagtgt kttttcatga attcggggtc tgagataata gatcgccacg    60
acttgcagac caagctactc ctcatcagtg atttagcagg a                        101

<210> SEQ ID NO 27
```

```
<211> LENGTH: 101
<212> TYPE: DNA
<213> ORGANISM: Daucus carota

<400> SEQUENCE: 27
ctctaatacc atttgtgttc taatatttct tgttcaggtc actttacttt gacatcctag      60
gtctggtgac ccgtttctaa gcttatctag tgatggttgt t                        101

<210> SEQ ID NO 28
<211> LENGTH: 71
<212> TYPE: DNA
<213> ORGANISM: Daucus carota

<400> SEQUENCE: 28
atccctgtca gaaaattgtt acgtcggaaa agaaggcttc acgacgcgat cggaggagct      60
gtagtaagag t                                                          71

<210> SEQ ID NO 29
<211> LENGTH: 101
<212> TYPE: DNA
<213> ORGANISM: Daucus carota

<400> SEQUENCE: 29
gcaagtatta cccaaaattg gccccaatat atattttttg tatccggcta cattgattgc      60
accaatgtca caatcttgac cawgaaaaaa gactcccttta a                       101

<210> SEQ ID NO 30
<211> LENGTH: 101
<212> TYPE: DNA
<213> ORGANISM: Daucus carota

<400> SEQUENCE: 30
tgtacgatat atgttcagtc tgttcttgag cctgatttta cacaatcttt aaatccgcgc      60
tggaaaaatg aaactttaga aggttttctt tgatctctta a                        101
```

UNITED STATES PATENT AND TRADEMARK OFFICE
CERTIFICATE OF CORRECTION

PATENT NO. : 10,704,058 B2
APPLICATION NO. : 16/078124
DATED : July 7, 2020
INVENTOR(S) : Adriana Dorien Haarsma et al.

It is certified that error appears in the above-identified patent and that said Letters Patent is hereby corrected as shown below:

On the Title Page

Column 1, Item (72) Inventors, Line 5, delete "Martinus," and insert -- Martinus Wijnker, --

Signed and Sealed this
Seventeenth Day of November, 2020

Andrei Iancu
*Director of the United States Patent and Trademark Office*